(12) United States Patent
Murakami et al.

(10) Patent No.: US 11,692,302 B2
(45) Date of Patent: Jul. 4, 2023

(54) SIZING AGENT COMPOSITION, METHOD FOR PRODUCING CARBON FIBERS, AND CARBON FIBERS EACH HAVING SIZING AGENT APPLIED THEREONTO

(71) Applicant: TEIJIN LIMITED, Osaka (JP)

(72) Inventors: Takuya Murakami, Osaka (JP); Masayuki Chokai, Osaka (JP); Yuki Suzuki, Osaka (JP); Takeshi Naito, Osaka (JP)

(73) Assignee: TEIJIN LIMITED, Osaka (JP)

( * ) Notice: Subject to any disclaimer, the term of this patent is extended or adjusted under 35 U.S.C. 154(b) by 248 days.

(21) Appl. No.: 16/971,070

(22) PCT Filed: Feb. 14, 2019

(86) PCT No.: PCT/JP2019/005193
§ 371 (c)(1),
(2) Date: Aug. 19, 2020

(87) PCT Pub. No.: WO2019/163616
PCT Pub. Date: Aug. 29, 2019

(65) Prior Publication Data
US 2021/0071356 A1     Mar. 11, 2021

(30) Foreign Application Priority Data

Feb. 21, 2018   (JP) .................................. 2018-028978

(51) Int. Cl.
| | | |
|---|---|---|
| *C08K 3/04* | (2006.01) | |
| *D06M 13/395* | (2006.01) | |
| *C07C 265/14* | (2006.01) | |
| *C08K 5/29* | (2006.01) | |
| *C08K 9/04* | (2006.01) | |
| *D06M 101/40* | (2006.01) | |

(52) U.S. Cl.
CPC ......... *D06M 13/395* (2013.01); *C07C 265/14* (2013.01); *C08K 3/04* (2013.01); *C08K 5/29* (2013.01); *C08K 9/04* (2013.01); *D06M 2101/40* (2013.01)

(58) Field of Classification Search
CPC .......... D06M 13/395; D06M 2101/40; D06M 2200/40; D06M 13/17; D06M 13/175; D06M 13/246; D06M 13/148; D06M 15/27; C07C 265/14; C08K 3/04; C08K 5/29; C08K 9/04; D01F 11/14; D01F 11/16; B29B 15/08

USPC ......................................................... 523/205
See application file for complete search history.

(56) References Cited

U.S. PATENT DOCUMENTS

| 2008/0160281 | A1* | 7/2008 | Vickery ............. | C08G 18/8061 |
| | | | | 65/480 |
| 2012/0276383 | A1* | 11/2012 | Hirano ............... | C08G 18/6674 |
| | | | | 428/368 |

FOREIGN PATENT DOCUMENTS

| EP | 0 965 679 A1 | 12/1999 |
| JP | 56-167715 A | 12/1981 |
| JP | 02-84558 A | 3/1990 |
| JP | 2000-355884 A | 12/2000 |
| JP | 2004-300267 A | 10/2004 |
| JP | 2005-290615 A | 10/2005 |
| JP | 2005-530878 A | 10/2005 |
| JP | 2006-144168 A | 6/2006 |
| WO | 2016/043043 A1 | 3/2016 |

OTHER PUBLICATIONS

English Translation of JP 2005290615 (Year: 2005).*
International Search Report for PCT/JP2019/005193, dated May 7, 2019.
European Search Report dated Mar. 15, 2021 in European Application No. 19758093.9.
International Preliminary Report on Patentability with Translation of Written Opinion of the International Searching Authority dated Aug. 27, 2020 in International Application No. PCT/JP2019/005193.

* cited by examiner

*Primary Examiner* — Hannah J Pak
(74) *Attorney, Agent, or Firm* — Sughrue Mion, PLLC

(57) ABSTRACT

An object of the present invention is to provide a sizing agent composition that gives a carbon fiber from which a carbon fiber-reinforced composite material having excellent adhesion between a resin and the carbon fiber and having excellent mechanical properties can be formed. The sizing agent composition of the invention is a sizing agent composition comprising (A) a blocked isocyanate, and (B) a compound containing at least one polar group and at least one unsaturated group per molecule. In the invention, the mixing ratio (mass ratio) of the blocked isocyanate (A) and the compound (B) containing at least one polar group and at least one unsaturated group per molecule (A/B) is preferably 95/5 to 5/95. In the invention, the blocked isocyanate (A) is preferably a compound having an aliphatic skeleton.

6 Claims, No Drawings

SIZING AGENT COMPOSITION, METHOD FOR PRODUCING CARBON FIBERS, AND CARBON FIBERS EACH HAVING SIZING AGENT APPLIED THERETO

CROSS REFERENCE TO RELATED APPLICATIONS

This application is a National Stage of International Application No. PCT/JP2019/005193 filed Feb. 14, 2019, claiming priority based on Japanese Patent Application No. 2018-028978 filed Feb. 21, 2018.

TECHNICAL FIELD

The present invention relates to a sizing agent composition for use in a carbon fiber, and a method for producing a carbon fiber and a sizing agent-applied carbon fiber each using the sizing agent composition. More particularly, the present invention is concerned with a sizing agent composition which can provide a composite material having excellent adhesion between a matrix resin and a carbon fiber, wherein the composite material has a radically polymerizable curable resin, such as an unsaturated polyester or vinyl ester resin, as a matrix resin.

BACKGROUND ART

Carbon fibers are lightweight and have excellent specific strength and specific modulus, and further have excellent heat resistance and chemical resistance, and therefore are used in the form of a fiber-reinforced composite material, which is a combination of the carbon fiber and various types of matrix resins, in many fields of aircraft members, aerospace members, automotive members, vessel members, civil engineering and building materials, sports goods, and the like. As the carbon fibers are being applied to a wide variety of uses, demands for carbon fibers having high performance are increasing, and particularly, carbon fibers for sports goods and aircraft members are required to have higher strength and higher modulus.

With respect to the composite material using a carbon fiber, for fully utilizing excellent properties of the carbon fiber, it is important that the adhesion between the carbon fiber and a matrix resin is excellent. However, the carbon fiber cannot always exhibit satisfactory adhesion to a matrix resin, and, for activating the surface of the carbon fiber, the carbon fiber has been subjected to surface oxidation treatment, such as chemical oxidation treatment, gas phase oxidation treatment, or electrolytic oxidation treatment. In the carbon fiber having a higher modulus, however, an activation reaction is unlikely to be caused on the surface of the carbon fiber in the surface oxidation treatment, and there is a need for an improvement of the adhesion between the carbon fiber and the matrix resin.

On the other hand, the carbon fiber has properties such that the elongation is small and the fiber is brittle, and hence a carbon fiber bundle which is a bundle of continuous carbon fibers is likely to cause fuzzing due to mechanical friction or the like. For this reason, for the purpose of suppressing the occurrence of fuzzing and the like, in the production process for a carbon fiber or a carbon fiber-reinforced composite material, the carbon fiber is subjected to sizing treatment in which a sizing agent is applied to the carbon fiber. By imparting a bundling property to the carbon fiber by the sizing treatment, it is possible to suppress fuzzing. With respect to the sizing treatment which has conventionally been made for the purpose of suppressing the occurrence of fuzzing and the like, recently, studies are made in an attempt to add an effect of improving the adhesion between the carbon fiber and a matrix resin to the sizing treatment.

For improving the adhesion between a carbon fiber and a matrix resin, for example, PTL 1 has proposed the use of a compound having both a terminal unsaturated group and a polar group as a sizing agent, and PTL 2 has proposed the use of a compound having an epoxy group and a vinyl group per molecule. However, satisfactory adhesion between the carbon fiber and the matrix resin cannot be achieved by using these compounds. Therefore, a sizing agent which can improve the adhesion between the carbon fiber and the matrix resin is desired.

SUMMARY OF INVENTION

Technical Problem

An object of the present invention is to improve the conventional techniques having the above-mentioned drawbacks and to provide a sizing agent composition that gives a carbon fiber from which a carbon fiber-reinforced composite material having excellent adhesion between a resin and the carbon fiber and having excellent mechanical properties can be formed.

Solution to Problem

The sizing agent composition of the invention is a sizing agent composition comprising (A) a blocked isocyanate, and (B) a compound containing at least one polar group and at least one unsaturated group per molecule. In the invention, it is preferred that the mixing ratio (mass ratio) of the blocked isocyanate (A) and the compound (B) containing at least one polar group and at least one unsaturated group per molecule (A/B) is 95/5 to 5/95.

In the invention, the blocked isocyanate (A) is preferably a compound having an aliphatic skeleton. Further, the compound (B) containing at least one polar group and at least one unsaturated group per molecule is preferably an ester compound of a polyol and an unsaturated carboxylic acid, more preferably an ester compound of a polyalkylene glycol and an unsaturated carboxylic acid.

The invention encompasses a method for producing a carbon fiber, comprising applying the above-mentioned sizing agent of the invention to a carbon fiber, and a carbon fiber obtained by the method, and a carbon fiber composite material comprising the carbon fiber and a matrix resin.

Advantageous Effects of Invention

By using the sizing agent composition of the invention, the adhesion between a fiber and a matrix resin is improved, so that a fiber-reinforced composite material having excellent mechanical properties can be obtained.

The carbon fiber of the invention has excellent adhesion to a matrix resin, and therefore, when the carbon fiber bundle in the invention is used as a reinforcing fiber for a fiber-reinforced composite material, a fiber-reinforced composite material having excellent mechanical properties can be obtained.

DESCRIPTION OF EMBODIMENTS

The sizing agent composition of the invention is a sizing agent composition comprising (A) a blocked isocyanate, and (B) a compound containing at least one polar group and at least one unsaturated group per molecule.

In the invention, the blocked isocyanate means a compound having an isocyanate group blocked by a blocking agent, wherein when the compound is heated, the blocking agent which blocks the isocyanate group is deblocked to generate an active isocyanate. In the invention, the blocked isocyanate (A) is preferably a blocked isocyanate compound comprising an isocyanate having two or more isocyanate groups.

By using such a blocked isocyanate in combination with the compound (B) containing at least one polar group and at least one unsaturated group per molecule, satisfactory storage stability of the sizing agent composition can be obtained. Further, by applying the sizing agent composition to a fiber and then heating it to a specific temperature or higher, the isocyanate group of the compound (A), the polar group of the compound (B), and the functional group on the surface of the fiber can be reacted with each other with intended timing to form a covalent bond (crosslinked structure), making it possible to cover the surface of the fiber with a reaction product having an unsaturated group. By virtue of this, the adhesion between the fiber and a matrix resin, particularly a radically reactive matrix resin, such as an unsaturated polyester or vinyl ester resin, is improved, so that a fiber-reinforced composite material having excellent mechanical properties can be obtained.

In the invention, the mixing ratio of the blocked isocyanate (A) and the compound (B) containing at least one polar group and at least one unsaturated group per molecule (A/B) is preferably 95/5 to 5/95.

In the invention, the blocked isocyanate (A) is preferably a compound having an aliphatic skeleton. With respect to the isocyanate compound which is a precursor of the blocked isocyanate (A) used in the invention, there is no particular limitation, but examples of the isocyanate compounds include polyisocyanates, such as an alkylene diisocyanate, dimethyldiphenyl diisocyanate, tolylene diisocyanate, metaphenylene diisocyanate, diphenylmethane diisocyanate, polymethylenepolyphenyl isocyanate, and triphenylmethane triisocyanate, and a polyol adduct polyisocyanate containing a terminal isocyanate group, which is obtained by reacting the above polyisocyanate and a compound having two or more active hydrogen atoms, such as trimethylolpropane or pentaerythritol, in a molar ratio such that the ratio of the isocyanate group (—NCO) and the hydroxyl group (—OH) is more than 1. Of these, a compound having an aliphatic skeleton, such as an alkylene diisocyanate, is preferred because the degree of freedom of the molecular chain after the crosslinking reaction is high, and appropriate binding force for the fibers (single fibers) is applied, so that both excellent handling properties of the fiber and excellent adhesion to a matrix resin can be easily achieved.

In the invention, the deblocking temperature of the blocking agent which blocks the isocyanate group of the blocked isocyanate (A) is preferably 50 to 250° C., more preferably 100 to 200° C., further preferably 120 to 180° C. Examples of blocking agents which are deblocked at such temperatures include oximes, such as methyl ethyl ketoxime, acetoxime, and cyclohexanoxime, lactams, such as ε-caprolactam, acetylacetone, phenols, and mercaptan. As the blocking agent, oximes, such as methyl ethyl ketoxime, acetoxime, and cyclohexanoxime, are especially preferably used because they can be removed under relatively simple conditions.

In the invention, with respect to the polar group contained in the compound (B) containing at least one polar group and at least one unsaturated group per molecule, there is no particular limitation as long as the polar group is a functional group capable of reacting with an isocyanate group, and, for example, there can be mentioned a hydroxyl group, an amino group, a phenol group, a lactam group, and an epoxy group. When the nucleophilicity of the polar group is too high, the resultant sizing agent composition is likely to be poor in the stability. Therefore, from the viewpoint of the stability of the sizing agent composition, the polar group is preferably a hydroxyl group, a phenol group, or an epoxy group.

The compound (B) containing at least one polar group and at least one unsaturated group per molecule is preferably a compound having 1 to 5 polar groups per molecule, more preferably a compound having 1 to 3 polar groups per molecule. The number of the unsaturated group or groups is preferably 1 to 5, and a compound having a terminal unsaturated group is preferred. The compound (B) preferably has a number average molecular weight of 100 to 2,000, more preferably 200 to 1,000, especially preferably 300 to 800. When the number average molecular weight of the compound (B) is in the above range, the compound (B) is readily reacted with the blocked isocyanate, making it possible to improve the adhesion between a fiber and a matrix resin. Further, an occurrence of fuzzing of the fiber is suppressed, so that a reinforcing fiber having excellent handling properties can be obtained. When the number average molecular weight of the compound (B) is too small, it is likely that the compound (B) easily evaporates at a temperature lower than the deblocking temperature for the blocked isocyanate. On the other hand, when the number average molecular weight of the compound (B) is too large, it is likely that the reaction site density is reduced. Therefore, in both the case where the number average molecular weight of the compound (B) is too small and the case where the number average molecular weight of the compound (B) is too large, the reactivity with the blocked isocyanate is likely to be reduced.

The compound (B) containing at least one polar group and at least one unsaturated group per molecule is preferably an ester compound of a polyol and an unsaturated carboxylic acid. With respect to the polyol as a precursor of the ester compound of a polyol and an unsaturated carboxylic acid, there is no particular limitation as long as it is an organic compound having two or more hydroxyl groups, and the polyol may be an aliphatic compound or an aromatic compound, but preferred is an aliphatic compound, such as a linear aliphatic compound, a branched aliphatic compound, or an alicyclic compound, and more preferred is a polyalkylene glycol. When a polyalkylene glycol is used, the alkylene group is preferably an alkylene group having 1 to 6 carbon atoms, and the number of repeating of the alkylene glycol (polymerization degree) is preferably 1 to 20, more preferably 2 to 10.

With respect to the unsaturated carboxylic acid as a precursor of the ester compound of a polyol and an unsaturated carboxylic acid, there is no particular limitation as long as it is a fatty acid having at least one double bond (unsaturated group) in the hydrocarbon portion, but preferred is an unsaturated carboxylic acid having 3 to 20 carbon atoms including the carbon of the carboxylic acid, and more preferred is an unsaturated carboxylic acid having 3 to 10 carbon atoms. The number of the unsaturated group or groups is preferably 1 to 5. Further, preferred is a compound having a terminal unsaturated group in which two hydrogens are bonded to one of the carbons having a double bond. The number of the carboxylic acid group or groups is preferably 1 to 5. Examples of such unsaturated carboxylic acids include acrylic acid, methacrylic acid, crotonic acid, maleic acid, fumaric acid, and itaconic acid.

In the invention, for improving the fiber in handling properties, abrasion resistance, fuzzing resistance, and impregnation properties, an auxiliary component, such as a dispersant or a surfactant, may be added to the sizing agent composition.

By using the above-mentioned sizing agent composition of the invention, the adhesion between a fiber and a matrix resin is improved, so that a fiber-reinforced composite material having excellent mechanical properties can be obtained.

With respect to the reinforcing fiber on which the sizing agent composition of the invention is applied, there is no particular limitation, but, when the reinforcing fiber is used in the form of a fiber bundle which is a bundle of a plurality of filaments (single fibers), especially remarkable effects can be obtained. With respect to the number of filaments constituting the fiber bundle, in the invention, the state of a bundle of filaments in which the number of the filaments is 10 or more is defined as a fiber bundle, and the number of filaments constituting the fiber bundle is preferably 100 or more, further preferably 1,000 to 100,000. When the sizing agent-applied fiber is a carbon fiber, from the viewpoint of the productivity and the like, the number of filaments constituting the fiber bundle is preferably 3,000 to 80,000, further preferably in the range of from 6,000 to 50,000. When the number of filaments constituting the fiber bundle is small, it is likely that the flexibility of the fiber bundle is increased to improve the handling properties, but the productivity of the reinforcing fiber tends to be lowered. On the other hand, when the number of filaments constituting the fiber bundle is large, the production of the fiber bundle is likely to be difficult, and further the fiber tends not to be satisfactorily treated with the sizing agent.

With respect to the whole shape of the fiber bundle, the fiber bundle is preferably a flat fiber bundle. When the fiber bundle is a flat fiber bundle, the applied sizing agent and the matrix resin which is used later in producing the composite material are more easily diffused into the inside of the fiber bundle. The flatness of the fiber bundle (width/thickness of the fiber bundle) is 10 times or more, especially preferably in the range of from 50 to 400 times.

The fiber bundle preferably has a width of 5 mm or more, especially preferably in the range of from 10 to 100 mm. Further, with respect to the length of the fiber bundle, there is no particular limitation, and the fiber bundle may be a continuous fiber or a discontinuous fiber. When the fiber bundle is used in the form of a discontinuous fiber, the fiber length is preferably in the range of from 1 to 100 mm. Further, the fiber length is more preferably in the range of from 5 to 50 mm. When the fiber bundle is used in the form of a discontinuous fiber, from the viewpoint of the productivity, it is preferred that the sizing agent is applied to the continuous fiber bundle and then the resultant fiber bundle is cut into a fiber with a desired fiber length.

The fibers (single fibers) used in the invention preferably have an average diameter in the range of from 0.001 to 100 µm, more preferably in the range of from 3 to 20 µm. A further preferred range of the average diameter is 4 to 15 µm, and an especially preferred range of the average diameter is 5 to 10 µm. When the fiber diameter is too small, the fiber component is bulky and it is likely to be difficult to increase the volume fraction of the fiber. On the other hand, when the fiber diameter is too large, it is likely that a fiber having a high strength is difficult to obtain. When the fiber diameter is in the above range, a composite material having excellent mechanical properties can be obtained.

With respect to the method for applying the sizing agent composition of the invention on a reinforcing fiber, there is no particular limitation, but preferred is a method in which a sizing agent solution is prepared, and the sizing agent solution is applied on a fiber (sizing treatment). With respect to the solvent used for diluting the sizing agent composition, there is no particular limitation, but preferred is water. Further, preferred is a method in which the sizing agent composition is emulsified using a surfactant to prepare a sizing agent water emulsion, and sizing is conducted using the prepared emulsion.

When preparing a sizing agent water emulsion, with respect to the surfactant used in the emulsion, there is no particular limitation, and an anionic, cationic, or nonionic surfactant or the like can be used. Of these, a nonionic surfactant is preferred from the viewpoint of the emulsifying performance and the stability of the obtained emulsion.

Examples of nonionic surfactants include surfactants of a polyethylene glycol type (such as a higher alcohol ethylene oxide addition product, an alkylphenol ethylene oxide addition product, a fatty acid ethylene oxide addition product, and a propylene glycol ethylene oxide addition product), and surfactants of a polyhydric alcohol type (such as a fatty acid ester of glycerol, a sorbitol fatty acid ester, and a fatty acid alkanolamide).

Examples of emulsifying methods include a method using a batch having an agitating element, a method using a ball mill, a method using a shaker, and a method using a high-shear emulsifier, such as a Gaulin homogenizer.

Further, with respect to the surfactant, there is no particular limitation as long as the sizing agent composition can be emulsified, and the surfactant may be generally added in an amount of about 0.1 to 30% by mass.

As an example of the method for sizing treatment, there can be mentioned a method in which a fiber is contacted with the sizing agent solution. Specifically, there can be mentioned a touch roll method in which parts of rolls are immersed in the sizing agent solution to transfer the solution to the surface of the rolls, and then a fiber is contacted with the rolls to apply the aqueous sizing agent solution on the fiber, and an immersion method in which a fiber is directly immersed in the sizing agent solution and then, if necessary, passed through nip rolls to control the applied amount of the sizing agent solution.

Further, the method for removing the solvent from the fiber is not limited, and various means, such as a heat treatment, air-drying, and centrifugal separation, may be used in combination. From the viewpoint of the cost, a heat treatment is preferred, and, as a heating means for the heat treatment, for example, hot air, a hotplate, a roller, or an infrared heater can be used.

As examples of the fibers to which the sizing agent in the invention is applied, there can be mentioned various reinforcing fibers capable of reinforcing the matrix resin. Specifically, preferred examples include various inorganic fibers, such as a carbon fiber, a glass fiber, a ceramic fiber, and a silicon carbide fiber, and various organic fibers, such as an aromatic polyamide fiber (aramid fiber), a polyethylene fiber, a polyethylene terephthalate fiber, a polybutylene terephthalate fiber, a polyethylene naphthalate fiber, a polyarylate fiber, a polyacetal fiber, a polybenzoxazole fiber, a polyphenylene sulfide fiber, a polyketone fiber, and a polybenzimidazole fiber. Especially, the sizing agent composition of the invention can be preferably used in a carbon fiber, a glass fiber, or an aromatic polyamide fiber. The sizing agent composition of the invention exhibits especially remarkable effects when used for a carbon fiber which has particularly excellent specific strength and specific modulus and is particularly needed to have high adhesion to the matrix resin for obtaining a fiber-reinforced composite material being lightweight and having high strength.

The method for producing a carbon fiber, which is another embodiment of the invention, is a method for producing a carbon fiber, which comprises applying the above-mentioned sizing agent composition to a carbon fiber, and the sizing agent-applied carbon fiber which is still another embodiment of the invention is a carbon fiber having applied thereon the above-mentioned sizing agent composition of the invention. With respect to the carbon fiber constituting the carbon fiber of the invention, there is no particular limitation, and any carbon fiber, such as a pitch, rayon, or polyacrylonitrile (PAN) carbon fiber, can be used, but, in view of the operating properties, process passage, mechanical strength, and the like, a PAN carbon fiber is preferred. With respect to properties of the carbon fiber, such as a fineness and a strength, there is no particular limitation, and any known carbon fiber can be used without any limitation. The PAN carbon fiber can be produced by, for example, the method described below.

Precursor Fiber

The precursor fiber used in the method for producing a carbon fiber of the invention is preferably a PAN precursor fiber which is produced by spinning a spinning solution obtained by subjecting to homopolymerization or copolymerization a monomer containing acrylonitrile in an amount of 90% by mass or more, preferably 95% by mass or more, and another monomer in an amount of 10% by mass or less. Examples of other monomers include itaconic acid, an acrylate, and a methacrylate. The raw material fiber obtained after spinning is subjected to washing with water, drying, stretching, and oiling treatment to obtain a precursor fiber. In this instance, steam stretching is conducted so that the total stretch ratio becomes 5 to 15 times. In view of the production efficiency, the number of filaments of the precursor fiber is preferably 1,000 filaments or more, more preferably 6,000 filaments or more.

Oxidization Treatment

The obtained precursor fiber is subjected to preheat treatment at 200 to 260° C. and at a stretch ratio of 0.90 to 1.00 prior to oxidization treatment, and subsequently subjected to oxidization treatment in heated air at 200 to 260° C. for 10 to 100 minutes. In this treatment, generally, the stretch ratio is in the range of from 0.85 to 1.15, but, for obtaining a carbon fiber having high strength and high modulus, the stretch ratio is more preferably 0.95 or more. This oxidization treatment is conducted for changing the precursor fiber to an oxidized fiber having a fiber density of 1.34 to 1.38 g/cm3, and the tension (stretch ratio) during the oxidization treatment is not particularly limited.

First Carbonization Treatment

The obtained oxidized fiber can be subjected to carbonization employing a conventionally known method. For example, in a first carbonization furnace having a nitrogen gas atmosphere at 300 to 800° C., the oxidized fiber is subjected to first carbonization on the first stage under stretching while gradually increasing the temperature and controlling the tension of the oxidized fiber.

Second Carbonization Treatment

For further advancing the carbonization and advancing graphitization (increase of the crystallinity of carbon), in a second carbonization furnace having an atmosphere of an inert gas, such as nitrogen gas, at 800 to 1,600° C., the first carbonization-treated fiber is subjected to carbonization while gradually increasing the temperature and controlling the tension of the first carbonization-treated fiber.

In each carbonization furnace, when the fiber experiences a marked change of the temperature at around the inlet of the furnace, for example, the fiber is abruptly introduced to the highest temperature, a lot of surface defects or internal defects are disadvantageously generated. Further, when the residence time in the high temperature portion of the furnace is excessively long, the graphitization disadvantageously proceeds to too high an extent, so that the obtained carbon fiber is brittle. In the first carbonization treatment and second carbonization step, the treatment may be conducted while controlling the tension, if necessary, using a plurality of furnaces so as to achieve predetermined physical properties.

When a higher modulus is required, a graphitization treatment may be further conducted at a temperature as high as 2,000 to 3,000° C.

Surface Oxidation Treatment

It is preferred that the above-mentioned carbon fiber is subjected to surface oxidation treatment. The method for the surface treatment is not limited, but preferred is an electrolytic oxidation treatment in which an electrolytic treatment is performed in an electrolytic solution. By subjecting the carbon fiber to surface treatment, a functional group can be introduced to the surface of the carbon fiber, making it possible to improve the adhesion to the sizing agent and matrix resin.

When an electrolytic oxidation treatment is performed, the quantity of electricity applied to the carbon fiber may be appropriately controlled so that an intended amount of the functional group on the surface of the fiber is obtained, but the quantity of electricity applied to 1 g of the carbon fiber is preferably in the range of from 10 to 500 C (coulomb), more preferably in the range of from 20 to 200 C. By controlling the quantity of electricity applied to 1 g of the carbon fiber to be in the above range, the carbon fiber having excellent mechanical properties of fiber and having improved adhesion to a resin is easily obtained. On the other hand, when the quantity of electricity applied to 1 g of the carbon fiber is less than 10 C, the adhesion of the carbon fiber to a resin is likely to become poor, and, when the quantity of electricity is more than 500 C, the fiber strength is likely to be lowered due to the excess treatment.

As an electrolytic solution, an aqueous solution of an inorganic acid, an inorganic base, or an inorganic salt is preferably used. As an electrolyte, for example, a strong acid, such as sulfuric acid or nitric acid, is preferably used because the surface treatment has excellent efficiency. Further, as an electrolyte, for example, an inorganic salt, such as ammonium sulfate or sodium hydrogencarbonate, is preferably used because the resultant electrolytic solution has a small danger, as compared to the electrolytic solution using an inorganic acid or an inorganic base.

The electrolyte concentration of the electrolytic solution is preferably 0.1 N or more, more preferably 0.1 to 1 N.

When the electrolyte concentration is less than 0.1 N, it is likely that the electrolytic solution has a low electric conductivity so that it is unsuitable for electrolysis. On the other hand, when the electrolyte concentration is too high, the electrolyte tends to precipitate, causing the stability of the concentration to be poor.

When the temperature of the electrolytic solution is increased, the electric conductivity is improved, and therefore the treatment can be promoted. On the other hand, when the temperature of the electrolytic solution is higher than 40° C., a change of the concentration due to evaporation of water or the like occurs, making it difficult to provide uniform conditions without a change with time. Therefore, the temperature of the electrolytic solution is preferably 15 to 40° C.

Sizing Treatment

The carbon fiber which has been subjected to surface treatment is passed through a sizing solution so as to apply the above-mentioned sizing agent composition to the carbon fiber. The concentration of the sizing agent in the sizing solution is preferably 10 to 25% by mass, and the applied amount of the sizing agent is preferably 0.1 to 10% by mass, more preferably 0.2 to 5% by mass, further preferably 0.5 to 2% by mass. In the sizing agent applying treatment, generally, an emulsion method is used in which a carbon fiber is immersed in an aqueous emulsion obtained using an emulsifying agent or the like. For improving the carbon fiber in handling properties, abrasion resistance, fuzzing resistance, and impregnation properties, an auxiliary component, such as a dispersant or a surfactant, may be added to the sizing agent.

Drying Treatment

The carbon fiber obtained after the sizing treatment is subjected to drying treatment to evaporate water or the like which is the dispersing medium used in the sizing treatment, obtaining a carbon fiber having applied thereto the sizing agent. In drying, a hot-air dryer is preferably used. With respect to the drying temperature, there is no particular limitation, but, in the case of a general-purpose aqueous emulsion, the drying temperature is generally set to 100 to 180° C. The drying treatment may serve also as a heat treatment after removal of the dispersing medium, and, in the invention, after the drying step, a heat treatment step can be conducted. By conducting a heat treatment after the drying (removal of the dispersing medium), the isocyanate group of the compound (A), the polar group of the compound (B), and the functional group on the surface of the fiber can be reacted with each other to form a crosslinked structure, making it possible to cover the surface of the fiber with a reaction product having an unsaturated group. The temperature of the heat treatment after the drying (removal of the dispersing medium) is preferably the deblocking temperature of the blocking agent which blocks the isocyanate group of the blocked isocyanate (A) or higher, more preferably in the range of from the deblocking temperature to 300° C., especially preferably in the range of from the deblocking temperature +5° C. to 270° C.

The carbon fiber of the invention obtained as mentioned above has excellent adhesion to a matrix resin, and therefore, by using the carbon fiber of the invention as a reinforcing fiber for a fiber-reinforced composite material, a fiber-reinforced composite material having excellent mechanical properties can be obtained.

By using the thus obtained carbon fiber and a matrix resin in combination, a fiber-reinforced composite material can be obtained using a known means or method, such as autoclave molding, press molding, resin transfer molding, or filament winding molding.

The carbon fiber composite material which is still further another embodiment of the invention is a carbon fiber composite material comprising the above-mentioned carbon fiber and a matrix resin.

The carbon fiber used in the carbon fiber composite material of the invention is preferably used in the form of a reinforcing fiber material in a sheet form. As a material in a sheet form, there can be mentioned a fiber material that is arranged unidirectionally in a sheet form, a fiber material that is formed into a cloth, such as woven or knitted fabric or nonwoven fabric, and multi-axial woven fabric. When the carbon fiber is used in the form of nonwoven fabric, the nonwoven fabric may be nonwoven fabric formed from a continuous fiber, or nonwoven fabric formed from a discontinuous fiber. When the carbon fiber is used in the form of a reinforcing fiber material in a sheet form, the sheet-form reinforcing fiber material preferably has a fiber areal weight of 25 to 10,000 g/m2.

As the matrix resin, a thermosetting resin or a thermoplastic resin is used. Specific examples of thermosetting matrix resins include an epoxy resin, an unsaturated polyester resin, a phenolic resin, a vinyl ester resin, a cyanate resin, an urethane acrylate resin, a phenoxy resin, an alkyd resin, an urethane resin, a preliminary polymerization resin of a maleimide resin and a cyanate resin, a bismaleimide resin, a polyimide resin and a polyisoimide resin each having an acetylene end, and a polyimide resin having a nadic acid end. These can be used individually or in combination. Of these, especially preferred are an epoxy resin and a vinyl ester resin, which have excellent heat resistance, modulus, and chemical resistance. These thermosetting resins may contain a coloring agent or various additives generally used, or the like, in addition to a curing agent and a curing accelerator.

Examples of thermoplastic resins include a polypropylene, a polysulfone, a polyether sulfone, a polyether ketone, a polyether ether ketone, an aromatic polyamide, an aromatic polyester, an aromatic polycarbonate, a polyether imide, a polyarylene oxide, a thermoplastic polyimide, a polyamide, a polyamide-imide, a polyacetal, a polyphenylene oxide, a polyphenylene sulfide, a polyarylate, a polyacrylonitrile, a polyaramid, and a polybenzimidazole.

When the sizing agent composition of the invention and a thermosetting resin, particularly a radically reactive matrix resin, such as an unsaturated polyester or vinyl ester resin, are used in combination, the adhesion between the carbon fiber and the matrix resin can be further improved, so that a carbon fiber composite material having more excellent mechanical properties can be obtained.

The content of the resin composition in the composite material is 10 to 90% by weight, preferably 20 to 60% by weight, further preferably 25 to 45% by weight.

The thus obtained carbon fiber-reinforced composite material of the invention is a fiber-reinforced composite material having excellent adhesion between the fiber and the matrix resin and having excellent mechanical properties.

EXAMPLES

Hereinbelow, the present invention will be described in more detail with reference to the following Examples, which should not be construed as limiting the scope of the invention. The physical properties of the carbon fibers were measured in accordance with the methods descried below.

(1) Evaluation of Applied Amount of a Sizing Agent

An applied amount of a sizing agent was determined as follows. Two 1.0 m treated sizing agent-applied fiber bundles were taken, and heated to 550° C. at 10° C./minute in a nitrogen gas atmosphere, and then held the fiber at the that temperature for 10 minutes, and a weight loss was determined as an applied amount of the sizing agent by making a calculation according the following formula.

Applied amount of the sizing agent = $(a-b)/b \times 100$ [%]

a: Weight [g] of the fiber before treated by burning
b: Weight [g] of the fiber after treated by burning (2) Evaluation of Fuzz A sizing agent-applied carbon fiber bundle was allowed to travel between urethane sheets having placed thereon a weight of 125 g at a speed of 50 feet/minute for two minutes, and an amount of the carbon fiber remaining on the urethane sheets was measured, and a calculation was made according to the following formula. The Fuzz value is preferably 40 µg/ft or less, more preferably 30 µg/ft or less.

Fuzz value (µg/ft) =Amount (µg) of the fuzz captured/Length (ft) of the fiber bundle evaluated (3) Evaluation of MPF A sizing agent-applied carbon fiber bundle was allowed to travel, while applying a tension of 200 g to the carbon fiber bundle, through five pin guides at a speed of 50 feet/minute for two minutes, and then passed between urethane sheets having placed thereon a weight of 125 g, and an amount of the carbon fiber remaining on the urethane sheets was measured, and a calculation was made according to the following formula. The MPF value is preferably 60 µg/ft or less, more preferably 30 µg/ft or less.

MPF value (µg/ft) =Amount (µg) of the fuzz captured/Length (ft) of the fiber bundle evaluated (4) Contact Angle The wettability of a carbon fiber was evaluated by a contact angle.

A carbon fiber having a sizing agent applied thereto was evaluated by measuring a contact angle using the below-shown vinyl ester resin. Using Model DMs-401, manufactured by Kyowa Interface Science Co., Ltd., as a contact angle measurement apparatus, 2 µL of a droplet of the resin was placed on the sizing agent-applied carbon fiber bundle at room temperature, and a change of a contact angle of the resin with time was observed. The wettability was evaluated by a contact angle measured when it was in equilibrium.

(5) Interfacial Shear Strength (Microdroplet)

Using a matrix resin prepared from 100 parts by weight of the below-shown vinyl ester resin, 1 part by weight of a peroxide curing agent, and 0.5 part of cobalt naphthenate as a catalyst, an interfacial shear strength was measured by a microdroplet method.

Sizing Agent Composition

A sizing agent composition was prepared by appropriately mixing the following compounds as mentioned below.

Compound (A): Blocked Isocyanate

NBP-873D: NBP-873D (product name), manufactured by Meisei Chemical Works, Ltd.; hexamethylene diisocyanate trimer blocked by a methyl ethyl ketoxime group (aliphatic blocked isocyanate); isocyanate group content: 4; deblocking temperature=150° C.

NBP-211: NBP-211 (product name), manufactured by Meisei Chemical Works, Ltd.; polyol adduct polyisocyanate compound having a hexamethylene diisocyanate trimer blocked by a methyl ethyl ketoxime group and at least one ethylene glycol skeleton (aliphatic blocked isocyanate); isocyanate group content: 4; deblocking temperature=150° C.

Meikanate CX: Meikanate CX (product name), manufactured by Meisei Chemical Works, Ltd.; aliphatic blocked isocyanate; deblocking temperature=120 to 130° C.

Meikanate TP-10: Meikanate TP-10 (product name), manufactured by Meisei Chemical Works, Ltd.; aromatic blocked isocyanate; deblocking temperature=130° C.

Compound (B): Compound Containing at least One Hydroxyl Group (Polar Group) and at least One Unsaturated Group per Molecule PE-350: PE-350 (product name), manufactured by NOF Corporation; polyethylene glycol monomethacrylate; number average molecular weight: 478

Compounds Other than Compounds (A) and (B)

Diallyl isophthalate: Diallyl isophthalate, manufactured by Tokyo Chemical Industry Co., Ltd.

Vinyl ester: Ripox R-806 (product name), manufactured by Showa Denko K.K.; vinyl ester resin Example 1

NBP-873D as the blocked isocyanate (A) and PE-350 as the compound (B) containing a hydroxyl group and an unsaturated group per molecule were mixed in an effective component ratio (mass ratio) of 75/25 to prepare a sizing solution.

A polyacrylonitrile fiber was subjected to oxidization treatment in air at 250° C., and then subjected to low-temperature carbonization in a nitrogen gas atmosphere at the highest temperature of 650° C. Then, the resultant fiber was subjected to high-temperature carbonization in a nitrogen gas atmosphere at 1,300° C., and the thus produced carbon fiber was subjected to surface treatment by electrolytic oxidation using a 10 wt % aqueous solution of ammonium sulfate to obtain an unsized carbon fiber bundle (tensile strength: 4,300 MPa; tensile modulus: 240 GPa; the number of filaments: 24,000). The obtained unsized carbon fiber was continuously immersed in a sizing bath having the above-mentioned sizing agent diluted with water to apply the sizing agent to the carbon fiber so that the applied amount of the sizing agent became 1 wt %. Then, the resultant carbon fiber was subjected to heat treatment as well as water removal by means of a hot-air dryer at an atmosphere temperature of 160° C. to obtain a sizing agent-applied carbon fiber. The applied amount of the sizing agent was 1.06%. The obtained carbon fiber caused a very slight amount of fuzz and exhibited excellent handling properties. Further, the carbon fiber had a very high interfacial shear strength, and thus had very excellent adhesion to the resin.

A sizing treatment was conducted in the same manner as in Example 1 except that the temperature of the hot-air dryer was changed to 130° C. which is lower than the deblocking temperature of the blocking agent. With respect to the obtained sizing agent-applied carbon fiber, similar evaluation was performed. The carbon fiber obtained in the case where the heat treatment was conducted at 130° C. had an interfacial shear strength of 53 MPa, which was low as compared to that in Example 1.

Example 2

A sizing treatment was conducted in the same manner as in Example 1 except that NBP-211 was used as the blocked isocyanate, and that the ratio of the blocked isocyanate to PE-350 was changed to NBP-211/PE-350=75/25. The applied amount of the sizing agent was 1.05%. The obtained carbon fiber caused a slight amount of fuzz and exhibited excellent handling properties. Further, the carbon fiber had a very high interfacial shear strength, and thus had very excellent adhesion to the resin.

Example 3

A sizing treatment was conducted in the same manner as in Example 1 except that NBP-873D was used as the blocked isocyanate, and that the ratio of the blocked isocyanate to PE-350 was changed to NBP-873D/PE-350=50/50. The applied amount of the sizing agent was 0.88%. The obtained carbon fiber caused a very slight amount of fuzz and exhibited excellent handling properties. Further, the carbon fiber had a satisfactorily high interfacial shear strength, and thus had excellent adhesion to the resin.

Example 4

A sizing treatment was conducted in the same manner as in Example 1 except that NBP-211 was used as the blocked isocyanate, and that the ratio of the blocked isocyanate to PE-350 was changed to NBP-211/PE-350=50/50. The applied amount of the sizing agent was 1.11%. The obtained carbon fiber caused a very slight amount of fuzz and exhibited excellent handling properties. Further, the carbon fiber had a satisfactorily high interfacial shear strength, and thus had excellent adhesion to the resin.

Example 5

A sizing treatment was conducted in the same manner as in Example 1 except that Meikanate CX was used as the blocked isocyanate, and that the ratio of the blocked isocyanate to PE-350 was changed to Meikanate CX/PE-350=50/50. The applied amount of the sizing agent was 1.45%. The obtained carbon fiber caused a slight amount of fuzz and exhibited excellent handling properties. Further, the carbon fiber had a satisfactorily high interfacial shear strength, and thus had excellent adhesion to the resin.

Example 6

A sizing treatment was conducted in the same manner as in Example 1 except that Meikanate TP-10 was used as the blocked isocyanate. In Example 6 in which an aromatic isocyanate was used as the blocked isocyanate (A), the obtained carbon fiber caused a slightly large amount of fuzz, but had a high interfacial shear strength, and thus had excellent adhesion to the resin.

TABLE 1

|  |  |  | Example 1 | Example 2 | Example 3 | Example 4 | Example 5 | Example 6 |
|---|---|---|---|---|---|---|---|---|
| Sizing agent | Compound (A) |  | NBP-873D | NBP-211 | NBP-873D | NBP-211 | Meikanate CX | Meikanate TP-10 |
|  | Deblocking temperature | (° C.) | 150 | 150 | 150 | 150 | 130 | 130 |
|  | Compound (B) |  | PE-350 | PE-350 | PE-350 | PE-350 | PE-350 | PE-350 |
|  | A/B |  | 75/25 | 75/25 | 50/50 | 50/50 | 50/50 | 75/25 |
|  | Compound other than (A) and (B) |  | — | — | — | — | — | — |
| Fuzz |  | (μg/ft) | 24 | 40 | 27 | 14 | 1 | 38 |
| MPF |  | (μg/ft) | 28 | 45 | 22 | 20 | 58 | 85 |
| Contact angle |  | (°) | 1.9 | 2.6 | 2.8 | 7.4 | 6.9 | 5.7 |
| Interfacial shear strength |  | (MPa) | 84 | 81 | 67 | 67 | 67 | 65 |

Comparative Example 1

A sizing treatment was conducted in the same manner as in Example 1 except that diallyl isophthalate was used as a sizing agent. In Comparative Example 1 in which the blocked isocyanate (A) and the compound (B) containing a hydroxyl group and an unsaturated group per molecule were not used as a sizing agent, the obtained carbon fiber caused a large amount of fuzz and exhibited poor handling properties. Further, the carbon fiber had a low interfacial shear strength, as compared to that in Example 1, and thus had poor adhesion to the resin.

Comparative Example 2

A sizing treatment was conducted in the same manner as in Example 1 except that a vinyl ester resin, which is the same as the matrix resin, was used as a sizing agent. In Comparative Example 2 in which the blocked isocyanate (A) and the compound (B) containing a hydroxyl group and an unsaturated group per molecule were not used as a sizing agent, the obtained carbon fiber caused a large amount of fuzz and exhibited poor handling properties, and further had a low interfacial shear strength, as compared to that in Example 1, and thus had unsatisfactory adhesion to the resin.

Comparative Example 3

A sizing treatment was conducted in the same manner as in Example 1 except that, as a sizing agent, the compound (B) containing a hydroxyl group and an unsaturated group per molecule was not used, but only the blocked isocyanate (A) (NBP-873D) was used. In Comparative Example 3 in which the compound (B) containing a hydroxyl group and an unsaturated group per molecule was not contained as a sizing agent, the obtained carbon fiber caused a slight amount of fuzz and exhibited excellent handling properties, but had a low interfacial shear strength, as compared to that in Example 1, and thus had poor adhesion to the resin.

Comparative Example 4

A sizing treatment was conducted in the same manner as in Example 1 except that, as a sizing agent, the blocked isocyanate (A) was not used, but only the compound (B) containing a hydroxyl group and an unsaturated group per molecule (PE-350) was used. In Comparative Example 4 in which the blocked isocyanate (A) was not contained as a sizing agent, the obtained carbon fiber caused a large amount of fuzz, and had poor bundling property and hence exhibited unsatisfactory handling properties. Further, the carbon fiber had a low interfacial shear strength, as compared to that in Example 1, and thus had poor adhesion to the resin.

TABLE 2

|  |  | | Comparative Example 1 | Comparative Example 2 | Comparative Example 3 | Comparative Example 4 |
|---|---|---|---|---|---|---|
| Sizing agent | Compound (A) | | — | — | NBP-873D | — |
| | Deblocking temperature | (° C.) | — | — | 150 | — |
| | Compound (B) | | — | — | — | PE-350 |
| | A/B | | — | — | 100/0 | 0/100 |
| | Compound other than (A) and (B) | | Diallyl isophthalate | Vinyl ester | — | — |
| Fuzz | | (μg/ft) | 41 | 38 | 9 | 40 |
| MPF | | (μg/ft) | 62 | 102 | 10 | 74 |
| Contact angle | | (°) | 6.9 | 9.7 | 6 | 3.8 |
| Interfacial shear strength | | (MPa) | 41 | 53 | 60 | 58 |

INDUSTRIAL APPLICABILITY

The carbon fiber-reinforced composite material produced using a carbon fiber having applied thereto the sizing agent composition of the present invention has excellent adhesion to a matrix resin, and thus it is possible to obtain a carbon fiber-reinforced composite material having excellent mechanical physical properties.

CITATION LIST

Patent Literature

PTL 1: JP-A-2004-300267
PTL 2: JP-A-2000-355884

The invention claimed is:

1. A sizing agent composition comprising (A) a blocked isocyanate and (B) a compound containing at least one polar group and at least one unsaturated group per molecule, wherein the blocked isocyanate (A) is a compound having an aliphatic skeleton and the compound (B) containing at least one polar group and at least one unsaturated group per molecule is an ester compound of polyalkylene glycol and an unsaturated carboxylic acid,
wherein the blocked isocyanate (A) is selected from the group consisting of (i) hexamethylene diisocyanate trimer blocked by a methyl ethyl ketoxime group and (ii) polyol adduct polyisocyanate compound having a hexamethylene diisocyanate trimer blocked by a methyl ethyl ketoxime group and at least one ethylene glycol skeleton, and the mixing ratio (mass ratio) of the blocked isocyanate (A) and the compound (B) containing at least one polar group and at least one unsaturated group per molecule (AB) is 75/25 to 50/50.

2. A method for producing a sized carbon fiber, comprising applying the sizing agent composition according to claim 1 to a carbon fiber.

3. The method for producing a carbon fiber according to claim 2, wherein the sizing agent composition is applied to the carbon fiber, and then subjected to heat treatment at a temperature which is the deblocking temperature of a blocking agent for the blocked isocyanate (A) or higher.

4. The sizing agent composition according to claim 1, wherein the compound (B) is polyethylene glycol monomethacrylate.

5. The sizing agent composition according to claim 1, wherein the blocked isocyanate (A) is hexamethylene diisocyanate trimer blocked by a methyl ethyl ketoxime group.

6. The sizing agent composition according to claim 1, wherein the blocked isocyanate (A) is polyol adduct polyisocyanate compound having a hexamethylene diisocyanate trimer blocked by a methyl ethyl ketoxime group and at least one ethylene glycol skeleton.

* * * * *